United States Patent
Kudo et al.

(10) Patent No.: US 9,844,495 B2
(45) Date of Patent: Dec. 19, 2017

(54) SELF-ADHESIVE DENTAL COMPOSITE RESIN

(71) Applicant: KURARAY NORITAKE DENTAL INC., Kurashiki (JP)

(72) Inventors: Yasutaka Kudo, Nagoya (JP); Yamato Nojiri, Tainai (JP); Mitsuru Takei, Yokohama (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 15/317,421

(22) PCT Filed: Jun. 10, 2015

(86) PCT No.: PCT/JP2015/002916
§ 371 (c)(1),
(2) Date: Dec. 9, 2016

(87) PCT Pub. No.: WO2015/190101
PCT Pub. Date: Dec. 17, 2015

(65) Prior Publication Data
US 2017/0135910 A1    May 18, 2017

(30) Foreign Application Priority Data
Jun. 10, 2014 (JP) ................. 2014-119597

(51) Int. Cl.
| | |
|---|---|
| C08F 2/46 | (2006.01) |
| C08F 2/50 | (2006.01) |
| C08G 61/04 | (2006.01) |
| A61K 6/083 | (2006.01) |
| A61K 6/00 | (2006.01) |

(52) U.S. Cl.
CPC ............ A61K 6/083 (2013.01); A61K 6/0088 (2013.01)

(58) Field of Classification Search
CPC ............................. A61K 6/0088; A61K 6/083
USPC ......................................... 522/171, 1; 520/1
See application file for complete search history.

(56) References Cited

U.S. PATENT DOCUMENTS

| | | | |
|---|---|---|---|
| 5,300,537 A * | 4/1994 | Muller ..................... | A61L 24/06 433/228.1 |
| 5,741,543 A | 4/1998 | Winslow et al. | |
| 5,744,511 A | 4/1998 | Kazama et al. | |
| 6,953,832 B2 * | 10/2005 | Moszner .............. | A61K 6/0017 106/35 |
| 2009/0093563 A1 * | 4/2009 | Qian ..................... | A61K 6/0029 522/79 |
| 2010/0069524 A1 * | 3/2010 | Tanaka ................. | A61K 6/0023 522/171 |
| 2010/0130682 A1 | 5/2010 | Hinamoto et al. | |
| 2017/0135909 A1 * | 5/2017 | Takei ................... | A61K 6/0023 |

FOREIGN PATENT DOCUMENTS

| | | |
|---|---|---|
| EP | 2 153 811 A2 | 2/2010 |
| JP | 3-204846 A | 9/1991 |
| JP | 9-3109 A | 1/1997 |
| JP | 10-245525 A | 9/1998 |
| JP | 11-500152 A | 1/1999 |
| JP | 2002-212019 A | 7/2002 |
| JP | 2008-260752 A | 10/2008 |
| JP | 2013-209341 A | 10/2013 |
| WO | 96/24644 A1 | 8/1996 |
| WO | 2008/087977 A1 | 7/2008 |

OTHER PUBLICATIONS

International Search Report issued Aug. 25, 2015 in PCT/JP2015/002916 filed Jun. 10, 2015.

* cited by examiner

*Primary Examiner* — Jessica Whiteley
(74) *Attorney, Agent, or Firm* — Oblon, McClelland, Maier & Neustadt, L.L.P.

(57) ABSTRACT

The present invention provides a self-adhesive composite resin having excellent adhesiveness to tooth structures and excellent mechanical strength. The present invention relates to a self-adhesive dental composite resin containing: an asymmetric acrylamide-methacrylic acid ester compound (a); an acid group-containing (meth)acrylic polymerizable monomer (b); a hydrophobic crosslinkable polymerizable monomer (c); a photopolymerization initiator (d); and a filler (e). The asymmetric acrylamide-methacrylic acid ester compound (a) is represented by the following general formula (1):

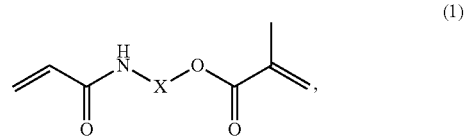

(1)

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$—, and R$^1$ is a hydrogen atom or an optionally substituted, linear or branched $C_1$ to $C_6$ aliphatic group.

11 Claims, No Drawings

SELF-ADHESIVE DENTAL COMPOSITE RESIN

TECHNICAL FIELD

The present invention relates to a self-adhesive dental composite resin. More specifically, the present invention relates to a self-adhesive dental composite resin having excellent adhesiveness to tooth structures and excellent mechanical strength.

BACKGROUND ART

Conventionally, in restorative treatment of dental caries and broken or chipped teeth caused by dental caries, dental adhesives and dental composite resins are generally used. Such restorative treatment is carried out according to the following procedure. First, caries is excavated to form a cavity, a dental adhesive is applied to the cavity, and then the adhesive thus applied is irradiated with visible light so as to cure the adhesive. Next, a dental composite resin is placed on the cured adhesive layer, and finally, the dental composite resin thus placed is irradiated with visible light so as to cure the resin.

In the above-described restoration method, two materials, i.e., a dental adhesive and a dental composite resin, are used. Recently, self-adhesive dental composite resins having self-adhesive properties have been developed and practically used as materials usable for restorative treatment with fewer steps and without the use of a dental adhesive.

Such a self-adhesive composite resin contains an acid group-containing polymerizable monomer, which is a component conventionally used in a dental adhesive to impart adhesiveness to tooth structures, in addition to components conventionally used in a dental composite resin, such as a crosslinkable polymerizable monomer and a filler, to provide mechanical strength and a polymerization initiator to improve curability (for example, Patent Literatures 1 and 2).

(Meth)acrylates are generally used as such polymerizable monomers. For example, in Patent Literatures 1 and 2, a crosslinkable polymerizable monomer having a hydroxyl group is used to increase bond strength.

CITATION LIST

Patent Literature

Patent Literature 1: JP 2008-260752 A
Patent Literature 2: EP 2153811 A2

SUMMARY OF INVENTION

Technical Problem

However, the compositions disclosed in Patent Literatures 1 and 2 have the following disadvantages. In the case where the composition disclosed in Patent Literature 1 is used as a self-adhesive composite resin to be applied directly to a tooth structure without using a dental adhesive, the mechanical strength is insufficient while the adhesiveness to the tooth structure is good. In the case where the composition disclosed in Patent Literature 2 is used as a self-adhesive composite resin to be applied directly to a tooth structure without using a dental adhesive, the adhesiveness to the tooth structure is insufficient while the mechanical strength is good. This means that no self-adhesive composite resin having both excellent adhesiveness to tooth structures and excellent mechanical strength has been found.

It is therefore an object of the present invention to provide a self-adhesive composite resin having excellent adhesiveness to tooth structures and excellent mechanical strength.

Solution to Problem

The present invention that has solved the above-described problems is a self-adhesive dental composite resin containing:

an asymmetric acrylamide-methacrylic acid ester compound (a);

an acid group-containing (meth)acrylic polymerizable monomer (b);

a hydrophobic crosslinkable polymerizable monomer (c);

a photopolymerization initiator (d); and a filler (e), wherein the asymmetric acrylamide-methacrylic acid ester compound (a) is represented by the following general formula (1):

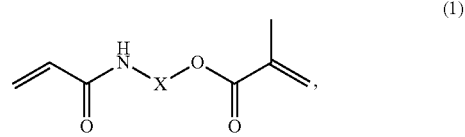

(1)

where X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$—, and R$^1$ is a hydrogen atom or an optionally substituted, linear or branched $C_1$ to $C_6$ aliphatic group.

In this self-adhesive dental composite resin, X in the above formula (1) representing the asymmetric acrylamide-methacrylic acid ester compound (a) is preferably an optionally substituted, linear or branched $C_1$ to $C_4$ aliphatic group. In this self-adhesive dental composite resin, the content of the asymmetric acrylamide-methacrylic acid ester compound (a) is preferably 2 to 30 parts by weight, the content of the acid group-containing (meth)acrylic polymerizable monomer (b) is preferably 1 to 40 parts by weight, and the content of the hydrophobic crosslinkable polymerizable monomer (c) is preferably 30 to 95 parts by weight in 100 parts by weight of the total polymerizable monomers. Furthermore, this self-adhesive dental composite resin preferably further contains a hydrophilic monofunctional polymerizable monomer (f). When the self-adhesive dental composite resin contains the hydrophilic monofunctional polymerizable monomer (f), the content of the hydrophilic monofunctional polymerizable monomer (f) is preferably 1 to 30 parts by weight. In this self-adhesive dental composite resin, an acid group in the acid group-containing (meth)acrylic polymerizable monomer (b) is preferably a phosphoric acid group or a carboxylic acid group. This self-adhesive dental composite resin is preferably a one-part self-adhesive dental composite resin.

Advantageous Effects of Invention

The self-adhesive dental composite resin of the present invention has excellent adhesiveness to tooth structures and excellent mechanical strength.

DESCRIPTION OF EMBODIMENTS

First, polymerizable monomer components in the self-adhesive dental composite resin of the present invention are described. As used in the present description, "(meth)acrylate" collectively refers to acrylate and methacrylate. The same applies to similar expressions.

The present invention is characterized in that an asymmetric acrylamide-methacrylic acid ester compound (a) represented by the above general formula (1) having two polymerizable groups, one of which is a methcrylic acid ester group and the other of which is an acrylamide group as a secondary amide group, is used (hereinafter, in the present description, a compound having two polymerizable groups bonded to a group represented by X, one of which is a methcrylic acid ester group and the other of which is an acrylamide group as a secondary amide group, is referred to as an "asymmetric acrylamide-methacrylic acid ester compound" for the sake of convenience).

It is not known exactly why a self-adhesive dental composite resin of the present invention containing an asymmetric acrylamide-methacrylic acid ester compound (a) exhibits high bond strength to dentin and has high mechanical strength. The reasons for this are probably as follows. The asymmetric acrylamide-methacrylic acid ester compound (a) used in the present invention has high hydrophilicity derived from amide protons and thus easily penetrates into the collagen layer of dentin. In addition, two polymerizable groups in the molecule of this compound (a), that is, an acrylamide group and a methacrylic acid ester group have relatively similar and balanced curing rates and thus the compound (a) exhibits sufficient curability and the penetrating self-adhesive dental composite resin forms a solid layer. In general, when an acrylic acid ester and a methacrylic acid ester have the same skeleton, the acrylic acid ester that has no methyl group and thus is sterically unhindered is more reactive than the methacrylic acid ester. The same applies to an acrylamide and a methacrylamide. Furthermore, the present inventors' studies have revealed that when a methacrylamide and a methcrylic acid ester have the same skeleton, the curing rate of the methacrylic acid ester tends to be higher than that of the methacrylamide. Therefore, when two polymerizable groups in the molecule are a methacrylic acid ester and a methacrylamide, the curing rate of the ester side tends to be higher than that of the amide side and thus their curing rates tend to be less balanced. Probably, in the asymmetric acrylamide-methacrylic acid ester compound (a), the curing rates between the ester side and the amide side is well balanced because an ester which is believed to have a higher curing rate is combined with a less reactive methacrylic group and an amide which is believed to have a lower curing rate is combined with a more reactive acrylic group. That is, the asymmetric acrylamide-methacrylic acid ester compound (a) can be considered as a compound having both high hydrophilicity derived from amide protons and high polymerization curability derived from two polymerizable groups having well-balanced curing rates.

For the reasons described above, a self-adhesive dental composite resin containing the asymmetric acrylamide-methacrylic acid ester compound (a) has not only high adhesiveness to dentin but also excellent mechanical strength. In addition, the asymmetric acrylamide-methacrylic acid ester compound (a) has an asymmetric structure and thus is less crystalline, is oily in nature, contains both an acrylamide group and a methacrylic acid ester group in the molecule, and thus has better compatibility with other polymerizable monomers.

The asymmetric acrylamide-methacrylic acid ester compound (a) used in the present invention is represented by the following general formula (1).

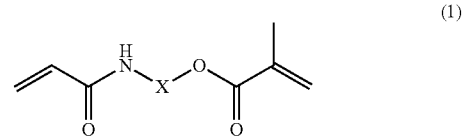

(1)

In this formula (1), X is an optionally substituted, linear or branched $C_1$ to $C_6$ aliphatic group or an optionally substituted aromatic group, and at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$— may be introduced into this aliphatic group. That is, the aliphatic group is optionally interrupted by at least one of the above-mentioned linking groups. $R^1$ is a hydrogen atom or an optionally substituted, linear or branched $C_1$ to $C_6$ aliphatic group.

X is a moiety for adjusting the hydrophilicity of the asymmetric acrylamide-methacrylic acid ester compound (a). The optionally substituted $C_1$ to $C_6$ aliphatic group represented by X may be a saturated aliphatic group (such as an alkylene group or a cycloalkylene group (for example, 1,4-cyclohexylene group)) or an unsaturated aliphatic group (such as an alkenylene group or an alkynylene group). In view of availability, ease of production, and chemical stability, it is preferable that the aliphatic group be a saturated aliphatic group (alkylene group). In view of adhesion to tooth structures and polymerization curability, X is preferably an optionally substituted, linear or branched $C_1$ to $C_4$ aliphatic group, and more preferably an optionally substituted, linear or branched $C_2$ to $C_4$ aliphatic group.

Examples of the $C_1$ to $C_6$ alkylene group include methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, tetramethylene, 1-butylethylene, 2-butylethylene, 1-ethyl-1-methylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, 1-butylethylene, 2-butylethylene, 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene, and hexamethylene groups. The $C_1$ to $C_6$ alkylene group is preferably a methylene, methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group, and more preferably a methylmethylene, ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene, or tetramethylene group.

Examples of the optionally substituted aromatic group represented by X include an aryl group and an aromatic heterocyclic group. An aryl group is more preferred than an aromatic heterocyclic group as the aromatic group mentioned above. The hetero ring of the aromatic heterocyclic group is usually unsaturated. The aromatic hetero ring is preferably a five-membered or six-membered ring. For example, a phenyl group is preferred as the aryl group. Examples of the aromatic heterocyclic group include furan, thiophene, pyrrole, oxazole, isoxazole, thiazole, isothiazole, imidazole, pyrazole, furazan, triazole, pyran, pyridine, pyridazine, pyrimidine, pyrazine, and 1,3,5-triazine groups. Among the aromatic groups mentioned above, a phenyl group is particularly preferred.

The aliphatic group as $R^1$ may be either a saturated aliphatic group (alkyl group) or an unsaturated aliphatic group (alkenyl or alkynyl group). In view of availability, ease of production, and chemical stability, the aliphatic group is preferably a saturated aliphatic group (alkyl group). Examples of the linear or branched $C_1$ to $C_6$ alkyl group as $R^1$ include methyl, ethyl, n-propyl, isopropyl, n-butyl, isobutyl, sec-butyl, tert-butyl, n-pentyl, isopentyl, sec-pentyl, neopentyl, tert-pentyl, 1-ethylpropyl, hexyl, isohexyl, 1,1-dimethylbutyl, 2,2-dimethylbutyl, 3,3-dimethylbutyl, and 2-ethylbutyl groups. The alkyl group is preferably a methyl, ethyl, n-propyl, isopropyl, n-butyl, isobutyl, sec-butyl, tert-butyl, or the like.

$R^1$ is more preferably a hydrogen atom or an optionally substituted, linear or branched $C_1$ to $C_4$ alkyl group, and even more preferably a hydrogen atom or an optionally substituted, linear or branched $C_1$ to $C_3$ alkyl group.

When the aliphatic group as X is interrupted by the above-mentioned linking group(s), the number of the linking groups is not particularly limited. The number of the linking groups may be about 1 to 10, preferably 1, 2, or 3, and more preferably 1 or 2. In the above formula (1), it is preferable that the aliphatic group as X be not interrupted by two or more contiguous linking groups. That is, it is preferable that the linking groups be not adjacent to each other. The linking group is more preferably at least one linking group selected from the group consisting of —O—, —S—, —CO—, —CO—O—, —O—CO—, —NH—, —CO—NH—, —NH—CO—, —CO—O—NH—, —O—CO—NH—, and —NH—CO—NH—, and particularly preferably at least one linking group selected from the group consisting of —O—, —S—, —CO—, —NH—, —CO—NH—, and —NH—CO—.

The substituent in the above formula (1) is not particularly limited. For example, the substituent is preferably a halogen atom (fluorine, chlorine, bromine, or iodine atom), a carboxy group, a hydroxy group, an amino group, an amino group mono- or di-substituted by $C_1$ to $C_6$ alkyl group(s), an acyl group, an acyloxy group, an amide group, a $C_1$ to $C_6$ alkoxycarbonyl group, a $C_1$ to $C_6$ alkoxy group, a $C_1$ to $C_6$ alkylthio group, a $C_1$ to $C_6$ alkyl group, or the like, and more preferably a halogen atom (fluorine, chlorine, bromine, or iodine atom), a $C_1$ to $C_6$ alkyl group, or the like. The $C_1$ to $C_6$ alkoxycarbonyl group, the $C_1$ to $C_6$ alkoxy group, the $C_1$ to $C_6$ alkylthio group, and the $C_1$ to $C_6$ alkyl group mentioned above may be substituted by 1, 2, or 3 halogen atoms. Specific examples of the above-mentioned alkyl group are the same as those of $R^1$, and a linear or branched $C_1$ to $C_4$ alkyl group is preferred. The number of the substituents is not particularly limited. The number of the substituents may be about 1 to 8, and preferably 1, 2, or 3.

The specific examples of the asymmetric acrylamide-methacrylic acid ester compound (a) are not particularly limited, and include the following.

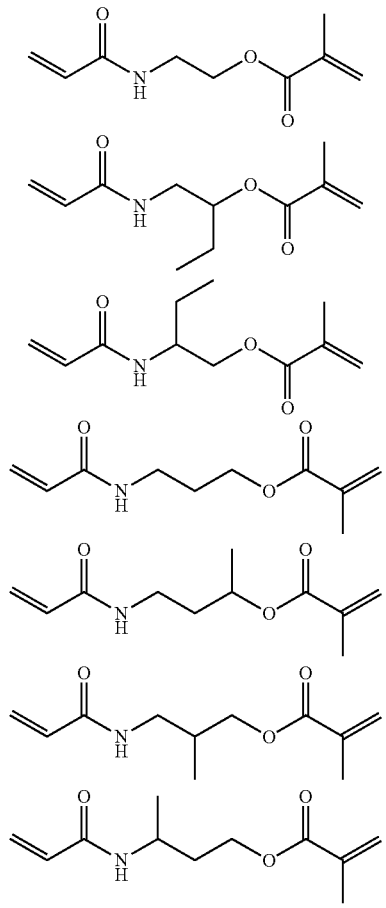

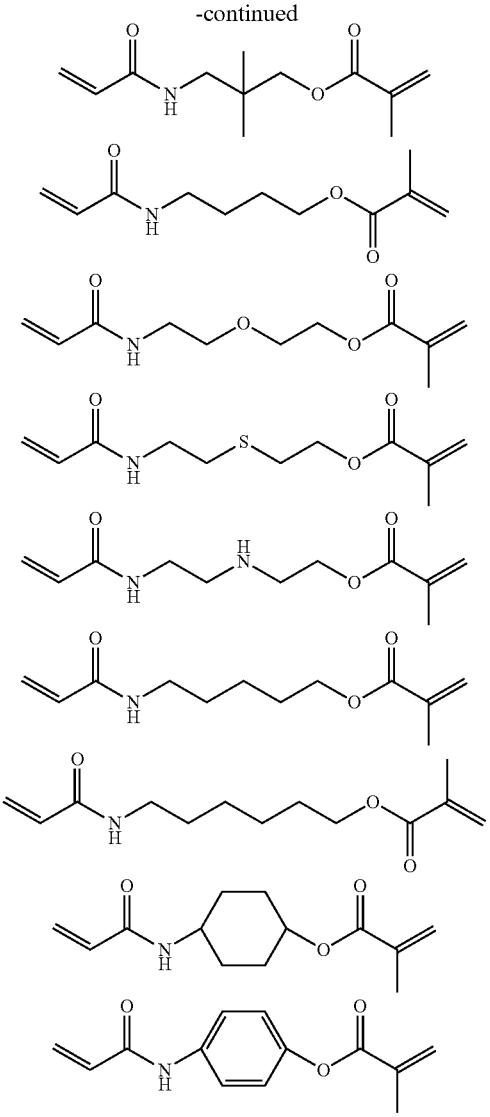

Among these, an asymmetric acrylamide-methacrylic acid ester compound having a linear or branched $C_2$ to $C_4$ aliphatic group as X is preferred in view of adhesion to tooth structures and polymerization curability. N-methacryloyloxyethyl acrylamide, N-methacryloyloxypropyl acrylamide, N-methacryloyloxybutyl acrylamide, N-(1-ethyl-(2-methacryloyloxy)ethyl) acrylamide, or N-(2-(2-methacryloyloxyethoxy)ethyl) acrylamide is more preferred. N-methacryloyloxyethyl acrylamide or N-methacryloyloxypropyl acrylamide is most preferred because of its high hydrophilicity responsible for penetration into the collagen layer of dentin.

One of the above-mentioned compounds may be contained alone as the asymmetric acrylamide-methacrylic acid ester compound (a), or a combination of two or more thereof may be contained as the asymmetric acrylamide-methacrylic acid ester compound (a). The content of the asymmetric acrylamide-methacrylic acid ester compound (a) is not particularly limited as long as the effect of the present invention can be obtained. The content of the asymmetric acrylamide-methacrylic acid ester compound (a) is preferably in the range of 2 to 30 parts by weight, more preferably in the range of 5 to 25 parts by weight, and most preferably in the range of 8 to 20 parts by weight in 100 parts by weight of the total polymerizable monomers in the self-adhesive dental composite resin.

Next, the acid group-containing (meth)acrylic polymerizable monomer (b) used in the present invention is described. In the present invention, the (meth)acrylic polymerizable monomer refers to a (meth)acrylate-based polymerizable monomer and/or a (meth)acrylamide-based polymerizable monomer.

The acid group-containing (meth)acrylic polymerizable monomer (b) is an essential component for the self-adhesive dental composite resin of the present invention to exhibit adhesiveness. The acid group-containing (meth)acrylic polymerizable monomer (b) has the effect of demineralizing tooth structures, and promotes the penetration of the asymmetric acrylamide-methacrylic acid ester compound (a) into dentin and binds to the tooth structures. The acid-group-containing (meth)acrylic polymerizable monomer (b) is a polymerizable monomer having at least one of acid groups such as a phosphoric acid group, a phosphonic acid group, a pyrophosphoric acid group, a carboxylic acid group, and a sulfonic acid group and having at least one of an acryloyl group, a methacryloyl group, an acrylamide group, and a methacrylamide group. In view of adhesion to tooth structures, the acid group-containing (meth)acrylic polymerizable monomer (b) is preferably a monofunctional monomer having at least one of the above-mentioned acid groups and having any one of an acryloyl group, a methacryloyl group, an acrylamide group, and a methacrylamide group, as a polymerizable group. Specific examples thereof are as follows.

Examples of the phosphoric acid group-containing (meth)acrylic polymerizable monomer include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl] hydrogen phosphate, bis[4-(meth)acryloyloxybutyl]hydrogen phosphate, bis[6-(meth)acryloyloxyhexyl] hydrogen phosphate, bis[8-(meth)acryloyloxyoctyl] hydrogen phosphate, bis[9-(meth)acryloyloxynonyl]hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl) hydrogen phosphate, and 2-(meth)acryloyloxypropyl-(4-methoxyphenyl) hydrogen phosphate; and their acid chlorides, alkali metal salts, ammonium salts, and amine salts.

Examples of the phosphonic acid group-containing (meth)acrylic polymerizable monomer include: 2-(meth)acryloyloxyethylphenyl phosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth)acryloyloxydecylphosphonoacetate; and their acid chlorides, alkali metal salts, ammonium salts, and amine salts.

Examples of the pyrophosphoric acid group-containing (meth)acrylic polymerizable monomer include: bis[2-(meth)acryloyloxyethyl] pyrophosphate, bis[4-(meth)acryloyloxybutyl] pyrophosphate, bis[6-(meth)acryloyloxyhexyl]pyrophosphate, bis[8-(meth)acryloyloxyoctyl] pyrophosphate, and bis[10-(meth)acryloyloxydecyl] pyrophosphate; and their acid chlorides, alkali metal salts, ammonium salts, and amine salts.

Examples of the carboxylic acid group-containing (meth)acrylic polymerizable monomer include: (meth)acrylic acid, 4-[2-[(meth)acryloyloxy]ethoxycarbonyl]phthalic acid, 4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and their acid anhydrides; and 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth)acryloyloxy-1,1-undecanedicarboxylic acid, and their acid chlorides, alkali metal salts, ammonium salts, and amine salts. Preferred among these are 4-(meth)acryloyloxyethyltrimellitic acid and its anhydrides.

Examples of the sulfonic acid group-containing (meth)acrylic polymerizable monomer include 2-(meth)acrylamide-2-methylpropanesulfonic acid, 2-sulfoethyl (meth)acrylate, and their acid chlorides, alkali metal salts, ammonium salts and amine salts.

Among these acid group-containing (meth)acrylic polymerizable monomers (b), the phosphoric, pyrophosphoric, or carboxylic acid group-containing (meth)acrylic polymerizable monomers are preferred since such monomers provide better bond strength to tooth structures. Particularly preferred are the phosphoric acid group-containing (meth)acrylic polymerizable monomers and the carboxylic acid group-containing (meth)acrylic polymerizable monomers. Among the phosphoric and carboxylic acid group-containing (meth)acrylic polymerizable monomers, a divalent phosphoric acid group-containing (meth)acrylic polymerizable monomer that has as the main chain of the molecule an alkyl or alkylene group having 6 to 20 carbon atoms and at least one carboxylic acid group-containing (meth)acrylic polymerizable monomer selected from the group consisting of 4-[2-[(meth)acryloyloxy]ethoxycarbonyl]phthalic acid, 4-[2-[(meth)acryloyloxy]ethoxycarbonyl]phthalic acid anhydride, 4-(meth)acryloyloxyethyltrimellitic acid, and 4-(meth)acryloyloxyethyltrimellitic acid anhydride are more preferable, and a divalent phosphoric acid group-containing (meth)acrylic polymerizable monomer that has as the main chain of the molecule an alkylene group having 8 to 12 carbon atoms, such as 10-methacryloyloxydecyl dihydrogen phosphate, is most preferable.

One of the above-mentioned monomers may be contained alone as the acid group-containing (meth)acrylic polymerizable monomer (b), or a combination of two or more thereof may be contained as the acid group-containing (meth)acrylic polymerizable monomer (b). The content of the acid group-containing (meth)acrylic polymerizable monomer (b) is not particularly limited as long as the effect of the present invention can be obtained. However, in order to obtain higher bond strength, the content of the acid group-containing (meth)acrylic polymerizable monomer (b) is preferably in the range of 1 to 40 parts by weight, more preferably in the range of 1 to 30 parts by weight, even more preferably in the range of 2 to 25 parts by weight, and particularly preferably in the range of 4 to 20 parts by weight in 100 parts by weight of the total polymerizable monomers.

Next, the hydrophobic crosslinkable polymerizable monomer (c) used in the present invention is described. The hydrophobic crosslinkable polymerizable monomer (c) is a hydrophobic compound having no acid group and having at least two polymerizable groups per molecule. As used herein, the term "hydrophobicity" refers to a solubility of less than 5 mass % in water at 25° C. The hydrophobic crosslinkable polymerizable monomer (c) has the effect of improving the handling properties and the mechanical strength of the self-adhesive dental composite resin of the present invention. Examples of the hydrophobic crosslinkable polymerizable monomer (c) include aromatic compound-based bifunctional polymerizable monomers, aliphatic compound-based bifunctional polymerizable monomers, and tri- or higher-functional polymerizable monomers.

Examples of the aromatic compound-based bifunctional polymerizable monomer include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane. Among these, 2,2-bis[4-(3-(methacryloyloxy-2-hydroxypropoxy)phenyl]propane (commonly known as "Bis-GMA"), 2,2-bis(4-(meth)acryloyloxyethoxyphenyl)propane, 2,2-bis(4-methacryloyloxypolyethoxyphenyl)propane (preferably having an average number of moles of added ethoxy groups of 2.6, commonly known as "D-2.6E"), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth)acryloyloxypentaethoxyphenyl)propane are preferable.

Examples of the aliphatic compound-based bifunctional polymerizable monomer include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, and 2,2,4-trimethylhexamethylene bis(2-carbamoyloxyethyl) di(meth)acrylate. Among these, triethylene glycol di(meth)acrylate, neopentyl glycol di(meth)acrylate, 1,2-bis(3-methacryloxy-2-hydroxypropoxy)ethane, 2,2,4-trimethylhexamethylene bis(2-carbamoyloxyethyl) dimethacrylate (commonly known as "UDMA") are preferable.

Examples of the tri- or higher-functional polymerizable monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(m- eth)acrylate, N,N-(2,2,4-trimethylhexamethylene)-bis[2-(aminocarboxy)propane-1,3-diol]tetra(meth)acrylate, and 1,7-diacryloyloxy-2,2,6,6-tetra(meth)acryloyloxymethyl-4-oxyheptane. Among these, N,N-(2,2,4-trimethylhexamethylene)-bis[2-(aminocarboxy)propane-1,3-diol]tetramethacrylate is preferable.

Among the above-mentioned hydrophobic crosslinkable polymerizable monomers (c), aromatic compound-based bifunctional polymerizable monomers and aliphatic compound-based bifunctional polymerizable monomers are preferably used in view of the mechanical strength and handling properties. Preferable examples of the aromatic compound-based bifunctional polymerizable monomers are 2,2-bis[4-(3-(methacryloyloxy-2-hydroxypropoxy)phenyl]propane (commonly known as "Bis-GMA") and 2,2-bis(4-methacryloyloxypolyethoxyphenyl)propane (preferably having an average number of moles of added ethoxy groups of 2.6, commonly known as "D-2.6E"). Preferable examples of the aliphatic compound-based bifunctional polymerizable monomers are glycerol di(meth)acrylate, triethylene glycol di(meth)acrylate, neopentyl glycol di(meth)acrylate, 1,6-hexanediol di(meth)acrylate, 1,10-decanediol di(meth)acrylate, 1,2-bis[3-methacryloxy-2-hydroxypropoxy]ethane, and 2,2,4-trimethylhexamethylene bis(2-carbamoyloxyethyl) dimethacrylate (commonly known as "UDMA").

Among the above-mentioned hydrophobic crosslinkable polymerizable monomers (c), Bis-GMA, D-2.6E, TEGDMA, and UDMA are more preferable, and Bis-GMA, D-2.6E, and TEGDMA are even more preferable.

One of the above-mentioned monomers may be contained alone as the hydrophobic crosslinkable polymerizable monomer (c), or a combination of two or more thereof may be contained as the hydrophobic crosslinkable polymerizable monomer (c). When the content of the hydrophobic crosslinkable polymerizable monomer (c) is too high, the penetrability of the composition into tooth structures may decrease and thus its bond strength may decrease. When the content of the hydrophobic crosslinkable polymerizable monomer (c) is too low, the effect of improving the mechanical strength may not be obtained sufficiently. Thus, the content of the hydrophobic crosslinkable polymerizable monomer (c) is in the range of 30 to 95 parts by weight, preferably in the range of 40 to 90 parts by weight, more preferably in the range of 50 to 85 parts by weight, and most preferably in the range of 60 to 80 parts by weight in 100 parts by weight of the total polymerizable monomers in the self-adhesive dental composite resin.

Preferably, the self-adhesive dental composite resin of the present invention further contains a hydrophilic monofuctional polymerizable monomer (f) as a polymerizable monomer component, but need not necessarily contain the hydrophilic monofunctional polymerizable monomer (f). The hydrophilic monofunctional polymerizable monomer (f) refers to a monofunctional polymerizable monomer, other than the asymmetric acrylamide-methacrylic acid ester compound (a) and the acid group-containing (meth)acrylic polymerizable monomer (b), having a solubility of 5 mass % or more in water at 25° C. The hydrophilic monofunctional polymerizable monomer (f) preferably has a solubility of 10 mass % or more, and more preferably a solubility of 15 mass % or more in water at 25° C. The hydrophilic monofunctional polymerizable monomer (f) thus contained contributes to higher bond strength to dentin.

The hydrophilic monofunctional polymerizable monomer (f) has a hydrophilic group such as a hydroxyl group, an oxymethylene group, an oxyethylene group, an oxypropylene group, or an amide group. Examples of the hydrophilic monofunctional polymerizable monomer (f) include: hydrophilic monofunctional (meth)acrylate-based polymerizable monomers such as 2-hydroxyethyl (meth)acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-trimethylammoniumethyl (meth)acrylchloride, and polyethylene glycol di(meth)acrylate (having 9 or more oxyethylene groups); and hydrophilic monofunctional (meth)acrylamide-based polymerizable monomers such as N-methylol (meth)acrylamide, N-hydroxyethyl (meth)acrylamide, N,N-(dihydroxyethyl) (meth)acrylamide, N-methoxymethyl (meth)acrylamide, N-ethoxymethyl (meth)acrylamide, diacetone (meth)acrylamide, 4-(meth)acryloylmorpholine, N-trihydroxymethyl-N-methyl (meth)acrylamide, and a monofunctional (meth)acrylamide-based polymerizable monomer represented by the following general formula (2).

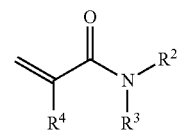

(2)

In the formula (2), $R^2$ and $R^3$ are each independently an optionally substituted, linear or branched $C_1$ to $C_3$ alkyl group, and $R^4$ is a hydrogen atom or a methyl group.

The same substituent in the formula (1) can be used as $R^2$ or $R^3$. Examples of the above-mentioned $C_1$ to $C_3$ alkyl group as $R^2$ or $R^3$ include a methyl group, an ethyl group, an n-propyl group, and an isopropyl group.

Among these hydrophilic monofunctional polymerizable monomers (f), in view of adhesion to tooth structures, 2-hydroxyethyl (meth)acrylate, 2,3-dihydroxypropyl (meth)acrylate, diacetone (meth)acrylamide, and hydrophilic monofunctional (meth)acrylamide-based polymerizable monomers are preferable, and a monofunctional (meth)acrylamide-based polymerizable monomer represented by the general formula (2) is more preferable. One of the above-mentioned monomers may be contained alone as the hydrophilic monofunctional polymerizable monomer (f), or a combination of two or more thereof may be contained as the hydrophilic monofunctional polymerizable monomer (f).

Among the monofunctional (meth)acrylamide-based polymerizable monomers represented by the general formula (2), in view of storage stability, N,N-dimethylacrylamide and N,N-diethylacrylamide are more preferable, and N,N-diethylacrylamide is most preferable.

In the present invention, when the content of the hydrophilic monofunctional polymerizable monomer (f) is too low, the effect of improving the bond strength may not be obtained sufficiently. When the content of the hydrophilic monofunctional polymerizable monomer (f) is too high, the mechanical strength may decrease. Thus, the content of the hydrophilic monofunctional polymerizable monomer (f) is preferably in the range of 1 to 30 parts by weight, more preferably in the range of 2 to 28 parts by weight, even more preferably in the range of 5 to 25 parts by weight, and particularly preferably in the range of 7 to 20 parts by weight in 100 parts by weight of the total polymerizable monomers in the self-adhesive dental composite resin.

The self-adhesive dental composite resin of the present invention may contain a polymerizable monomer other than the above-mentioned polymerizable monomers, i.e., the asymmetric acrylamide-methacrylic acid ester compound (a), the acid group-containing (meth)acrylic polymerizable monomer (b), the hydrophobic crosslinkable polymerizable monomer (c), and the hydrophilic monofunctional polymerizable monomer (f), in order to improve its bond strength, handling properties, and mechanical strength. The self-adhesive dental composite resin of the present invention may contain, as a polymerizable monomer, a hydrophilic multifunctional (meth)acrylate-based polymerizable monomer and/or a symmetric (meth)acrylamide compound or the like to the extent that the effect of the present invention is not impaired. However, it is preferable that the self-adhesive dental composite resin contain no such polymerizable monomer or compound (be substantially free of such a polymerizable monomer or a compound). In the present description, the phrase "being substantially free of a component" means that the self-adhesive dental composite resin of the present invention contains no such component or contains only traces of the component to the extent that the effect of the self-adhesive dental composite resin of the present invention is not impaired. Examples of the hydrophilic multifunctional (meth)acrylate-based polymeriszable monomer include pentaerythritol dimethacrylate, erythritol dimethacrylate, mannitol dimethacrylate, xylitol dimethacrylate, sorbitol dimethacrylate, and glycerol dimethacrylate. Examples of the symmetric (meth)acrylamide compound include bisacrylamide ethylene and N,N-diethyl-1,3-propylene-bisacrylamide.

Photopolymerization Initiator (d)

The photopolymerization initiator (d) is a component that promotes polymerization curing of a self-adhesive composite resin. The photopolymerization initiator (d) can be selected for use from photopolymerization initiators commonly used in the industrial field. Among them, photopolymerization initiators used in dental applications are preferably used. One of the photopolymerization initiators is used alone, or two or more of them are used in appropriate combination.

Examples of the photopolymerization initiator include (bis)acylphosphine oxides, water-soluble acylphosphine oxides, thioxanthones, quaternary ammonium salts of thioxanthones, ketals, α-diketones, coumarins, anthraquinones, benzoin alkyl ether compounds, and α-aminoketone compounds.

It is preferable to use, among these photopolymerization initiators, at least one selected from the group consisting of (bis)acylphosphine oxides, salts thereof, α-diketones, and coumarin compounds. The use of such a photopolymerization initiator makes it possible to obtain a self-adhesive composite resin that has excellent photocurability in the visible and near-ultraviolet regions and thus exhibits sufficiently high photocurability regardless of which light source among a halogen lamp, light-emitting diode (LED), and xenon lamp is used.

Examples of the acylphosphine oxide that may be used as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl) phosphonate. Preferred among these is 2,4,6-trimethylbenzoyldiphenylphosphine oxide.

Examples of the bisacylphosphine oxide that may be used as the photopolymerization initiator include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide. Preferred among these is bis-(2,4,6-trimethylbenzoyl)phenylphosphine oxide.

Examples of the α-diketones that may be used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Particularly preferred among these is camphorquinone, since it shows maximum absorption at a wavelength in the visible region Examples of the coumarin compounds that may be used as the photopolymerization initiator include compounds disclosed in JP 9-3109 A and JP 10-245525 A, such as 3,3'-carbonylbis(7-diethylaminocoumarin), 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3-benzoyl-8-methoxycoumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-8-methoxycoumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphto[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H,5H, 11H-[1]benzopyrano[6,7,8-ij]quinolizin-11-one. Preferred among them are 3,3'-carbonylbis(7-diethylaminocoumarin) and 3,3'-carbonylbis(7-dibutylaminocoumarin).

Specific examples of water-soluble acylphosphine oxides, thioxanthones, quaternary ammonium salts of thioxanthones, ketals, anthraquinones, benzoin alkyl ether compounds, and α-aminoketone compounds include those disclosed in WO 2008/087977 A1.

The content of the photopolymerization initiator (d) is not particularly limited. In view of the curability of the resulting self-adhesive composite resin, the content of the photopolymerization initiator (d) is preferably 0.001 to 20 parts by weight, more preferably 0.05 to 10 parts by weight, and even more preferably 0.1 to 5 parts by weight, with respect to 100 parts by weight of the total polymerizable monomers. When the content of the photopolymerization initiator (d) is less than 0.001 parts by weight, polymerization may not proceed sufficiently and thus bond strength may be reduced. Therefore, a content of 0.01 part by weight or more is more preferred. On the other hand, when the content of the photopolymerization initiator (d) is more than 20 parts by mass, if the polymerizability of the photopolymerization initiator itself is low, not only sufficient bond strength may not be obtained but also precipitation from the self-adhesive composite resin may occur. Therefore, a content of 10 parts by weight or less is more preferred, and a content of 5 parts by weight or less is even more preferred.

The self-adhesive composite resin of the present invention may further contain a chemical polymerization initiator. An organic peroxide is preferably used as the chemical polymerization initiator. The organic peroxide used as the chemical polymerization initiator is not particularly limited, and can be a commonly-known organic peroxide. Typical examples of the organic peroxide include ketone peroxides, hydroperoxides, diacyl peroxides, dialkyl peroxides, peroxyketals, peroxyesters, and peroxydicarbonates. Specific examples of the organic peroxides include those disclosed in WO 2008/087977 A1.

Filler (e)

The filler (e) is a component for improving the strength of the self-adhesive composite resin as a matrix or the handling properties of the self-adhesive composite resin as a paste.

As the filler (e), any known filler used in dental composite resins can be used without any limitation. Examples of the filler include: various types of glasses [containing silica as a main component and optionally containing oxides of heavy metals, boron, aluminum, etc., for example: glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and E-2000 and E-3000 manufactured by ESSTECH), strontium borosilicate glass (E-4000 manufactured by ESSTECH), lanthanum glass ceramics (GM 31684 manufactured by Schott), and fluoroaluminosilicate glass (GM 35429, G018-091, and GO 018-117 manufactured by Schott)]; various types of ceramics; composite oxides such as silica-titania and silica-zirconia; diatomaceous earth; kaolin; clay minerals (such as montmorillonite); activated white clay; synthetic zeolite; mica; calcium fluoride; ytterbium fluoride; yttrium fluoride; calcium phosphate; barium sulfate; zirconium dioxide; titanium dioxide; hydroxyapatite; and the like. These fillers may be used alone or in the form of a mixture of two or more of them. Among them, those containing silica as a main component (containing 25 mass % or more of silica, preferably 40 mass % or more of silica) are suitably used.

The average particle diameter of the filler (e) is preferably 0.1 to 50.0 umm, more preferably 0.2 to 20.0 μm, even more preferably 0.4 to 10.0 μm, and particularly preferably 0.5 to 4.5 μm. When the average particle diameter of the filler is within these ranges, sufficient mechanical strength can be obtained, and the paste does not become sticky and thus has good handling properties. In addition, the resulting cured product has high surface smoothness and gloss after polishing and good retention of the smoothness and gloss. In the present description, the average particle diameter of the filler means the average particle diameter of the primary particles of the filler (i.e., the average primary particle diameter).

The average particle diameter of the filler (e) can be determined by the laser diffraction scattering method. To be more specific, for example, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

It is desirable that the filler (e) be surface-treated with a surface treatment agent beforehand in order to improve the compatibility with the polymerizable monomer components or to increase the chemical bonding with the polymerizable monomer components so as to increase the mechanical strength of the cured product.

Examples of such a surface treatment agent include at least one organometallic compound selected from the group consisting of an organosilicon compound, an organotitanium compound, an organozirconium compound, and an organoaluminum compound. When two or more organometallic compounds are used, the resulting surface-treated layer may be composed of a mixture of the two or more organometallic compounds or may have a multilayer structure composed of two or more stacked layers respectively consisting of the organometallic compounds.

Examples of the organosilicon compounds include compounds represented by $(R^6)_n SiX_{4-n}$, where $R^6$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0, 1, 2 or 3. When there are two or more $R^6$ and two or more X, the two or more $R^6$ may be the same as or different from each other, and the two or more X may be the same as or different from each other.

Specific examples of the organosilicon compounds include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyltris(β-methoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl) γ-aminopropylmethyldimethoxysilane, N-β(aminoethyl) γ-aminopropyltrimethoxysilane, N-β(aminoethyl) γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyltrimethoxysilane (the number of carbon atoms between the (meth)acryloxy group and the silicon atom: 3 to 12, e.g., γ-methacryloxypropyltrimethoxysilane, etc.), and ω-(meth)acryloxyalkyltriethoxysilane (the number of carbon atoms between the (meth)acryloxy group and the silicon atom: 3 to 12, e.g., γ-methacryloxypropyltriethoxysilane, etc.).

Among those mentioned above, a coupling agent having a functional group copolymerizable with the polymerizable monomers described above is preferably used, and examples thereof include ω-(meth)acryloxyalkyltrimethoxysilane (the number of carbon atoms between the (meth)acryloxy group and the silicon atom: 3 to 12), ω-(meth)acryloxyalkyltriethoxysilane (the number of carbon atoms between the (meth)acryloxy group and the silicon atom: 3 to 12), vinyltrimethoxysilane, vinyltriethoxysilane, vinyltriacetoxysilane, and γ-glycidoxypropyltrimethoxysilane.

Examples of the organotitanium compounds include tetramethyl titanate, tetraisopropyl titanate, tetra-n-butyl titanate, butyl titanate dimer, and tetra(2-ethylhexyl) titanate.

Examples of the organozirconium compounds include zirconium isopropoxide, zirconium n-butoxide, zirconium acetylacetonate, and zirconyl acetate.

Examples of the organoaluminum compounds include aluminum acetylacetonate and a chelate compound of a salt of aluminum and an organic acid.

The shape of the filler (e) is not particularly limited. The shape of the filler (e) may be selected as appropriate for the properties of the dental composite resin that should be improved. Specifically, the filler in the form of an irregular-shaped or spherical powder can be used. When the irregular-shaped filler (e) is used, the mechanical strength and wear resistance are particularly improved. When the spherical filler (e) is used, the surface smoothness and gloss after polishing and the retention of the smoothness and gloss are particularly improved. In the present invention, a commercially available filler may be used as the filler (e).

The content of the filler (e) is not particularly limited as long as the effect of the present invention can be obtained. The content of the filler (e) is preferably in the range of 100 to 900 parts by weight, more preferably in the range of 150 to 600 parts by weight, and particularly preferably in the range of 200 to 450 parts by weight, with respect to 100 parts by weight of the total polymerizable monomers. When the content of the filler (e) is in these ranges, the resulting cured product has sufficient mechanical strength and sufficient paste handling properties. The content of the filler (e) is preferably 50 to 90 weight %, more preferably 60 to 86 weight %, and particularly preferably 65 to 85 weight %, with respect to the total weight of the self-adhesive dental composite resin.

The filler contained in the dental composite resin of the present invention may consist only of a filler having an average particle diameter of 0.1 to 50.0 μm, as described above. A filler having an average particle diameter of less than 0.1 μm (hereinafter referred to as an ultrafine particle filler) may also be used in combination with the filler having an average particle diameter of 0.1 to 50.0 μm in order to improve the paste handling properties. As such an ultrafine particle filler, any known inorganic ultrafine particles used in dental compositions can be used without any limitation. Preferred examples thereof include: ultrafine particles of inorganic oxides such as silica, alumina, titania, and zirconia; ultrafine particles of composite oxides of these oxides; and ultrafine particles of calcium phosphate, hydroxyapatite, yttrium fluoride, and ytterbium fluoride. More preferred are ultrafine particles of silica, alumina, titania, or the like which are prepared by flame pyrolysis. Examples of such ultrafine particles prepared by flame pyrolysis include those manufactured by Nippon Aerosil Co., Ltd. under the trade names of Aerosil, Aeroxide AluC, Aeroxide $TiO_2$ P25, Aeroxide $TiO_2$ P25S, VP Zirconium Oxide 3-YSZ, and VP Zirconium Oxide 3-YSZ PH.

The average particle diameter of the ultrafine particle filler is preferably 1 to 50 nm, and more preferably 5 to 40 nm. The average particle diameter of the ultrafine particle filler can be determined by electron microscopic observation. To be more specific about the electron microscopic observation, for example, the average particle diameter can be measured by taking a photograph of the particles with a scanning electron microscope (S-4000, manufactured by Hitachi, Ltd.) and measuring the particle diameters of (200 or more) particles observed in a unit area of field of view in the photograph by the use of an image-analyzing particle size distribution analysis software (MacView manufactured by Mountech Co., Ltd.). In this case, the particle diameter of each particle is obtained as an arithmetic mean value of the longest and shortest dimensions thereof, and the average primary particle diameter is calculated from the number of the particles and their particle diameters.

The ultrafine particle filler may be surface-treated beforehand with the surface treatment agent mentioned above in order to improve the compatibility with the polymerizable monomer components or to increase the chemical bonding with the polymerizable monomer components so as to increase the mechanical strength of the cured product.

When the ultrafine particle filler is used in combination with a filler having an average particle diameter of 0.1 to 50.0 μm, the content of the ultrafine particle filler is preferably 0.1 to 15 parts by weight, and more preferably 1 to 10 parts by weight with respect to 100 parts by weight of the total polymerizable monomers. When the content of the filler is 0.1 parts by weight or less, good paste handling properties may not be obtained. When the content of the filler is 10 parts by weight or more, the paste may be too viscous and thus good paste handling properties may not be obtained.

Next, optional components of the self-adhesive dental composite resin of the present invention are described.

Polymerization Accelerator (g)

In other embodiments, the photopolymerization initiator (d) and/or chemical polymerization initiator is used in combination with a polymerization accelerator (g). Examples of the polymerization accelerator (g) that may be used in the present invention include amines, sulfinic acids, sulfinates, borate compounds, barbituric acid derivatives, triazine compounds, copper compounds, tin compounds, vanadium compounds, halogen compounds, aldehydes, thiol compounds, sulfites, hydrogen sulfites, and thiourea compounds.

Amines that may be used as the polymerization accelerator (g) include aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferably used in view of the curability and storage stability of the self-adhesive dental composite resin, and in particular, N-methyldiethanolamine and triethanolamine are more preferably used.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3, 5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino) benzoate, propyl 4-(N,N-dimethylamino)benzoate, n-butoxyethyl 4-(N,N-dimethylamino)benzoate, 2-[methacryloyloxy]ethyl 4-(N,N-dimethylamino)benzoate, 4-(N,N-dimethylamino)benzophenone, and butyl 4-(N,N-dimethylamino)benzoate. Among these, at least one selected from the group consisting of N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino) benzophenone is preferably used in view of their ability to impart high curability to the self-adhesive dental composite resin.

Specific examples of the sulfinic acids, sulfinates, borate compounds, barbituric acid derivatives, triazine compounds, copper compounds, tin compounds, vanadium compounds, halogen compounds, aldehydes, thiol compounds, sulfites, hydrogen sulfites, and thiourea compounds include those disclosed in WO 2008/087977 A1.

One of the above-mentioned polymerization accelerators (g) may be used alone, or two or more thereof may be used in combination. The content of the polymerization accelerator (g) that may be used in the present invention is not particularly limited. In view of the curability, etc. of the resulting self-adhesive composite resin, the content of the polymerization accelerator (g) is preferably 0.001 to 30 parts by weight, more preferably 0.01 to 10 parts by weight, and most preferably 0.1 to 5 parts by weight, with respect to 100 parts by weight of the total polymerizable monomers. When the content of the polymerization accelerator (g) is less than 0.001 parts by weight, polymerization may not proceed sufficiently and thus adhesiveness may be reduced. Therefore, a content of 0.05 parts by weight or more is more preferred. On the other hand, when the content of the polymerization accelerator (g) is more than 30 parts by mass, if the polymerizability of the polymerization initiator itself is low, not only sufficient adhesiveness may not be obtained but also precipitation from the self-adhesive composite resin may occur. Therefore, a content of 20 parts by weight or less is more preferred.

Fluorine Ion-releasing Material (h)

The self-adhesive composite resin of the present invention may further contain a fluorine ion-releasing material (h). The self-adhesive composite resin containing the fluorine ion-releasing material (h) can impart acid resistance to tooth structures. Examples of the fluorine ion-releasing material include metal fluorides such as sodium fluoride, potassium fluoride, sodium monofluorophosphate, lithium fluoride, and ytterbium fluoride. One of these fluorine ion-releasing materials (h) may be contained alone, or two or more of them may be contained in combination.

Furthermore, the self-adhesive composite resin of the present invention may contain, for example, a pH adjuster, a polymerization inhibitor, an ultraviolet absorber, a thickener, a colorant, an antibacterial agent, or a flavor as long as the effect of the present invention is not impaired.

The self-adhesive dental composite resin of the present invention may preferably be a one-part or a multi-part self-adhesive dental composite resin. More preferred among these is a one-part type in view of the ease of handling.

A preferred embodiment of the self-adhesive dental composite resin of the present invention is, for example, a self-adhesive dental composite resin containing 2 to 30 parts by weight of the asymmetric acrylamide-methacrylic acid ester compound (a), 1 to 40 parts by weight of the acid group-containing (meth)acrylic polymerizable monomer (b), 30 to 95 parts by weight of the hydrophobic crosslinkable polymerizable monomer (c), and 1 to 30 parts by weight of the hydrophilic monofunctional polymerizable monomer (f) as an optional component in 100 parts by weight of the total polymerizable monomers, and further containing 0.001 to 20 parts by weight of the photopolymerization initiator (d), 100 to 900 parts by weight of the filler (e), and 0.001 to 30 parts by weight of the polymerization accelerator (g) as an optional component with respect to 100 parts by weight of the total polymerizable monomers.

A more preferred embodiment of the self-adhesive dental composite resin of the present invention is, for example, a self-adhesive dental composite resin containing 5 to 25 parts by weight of the asymmetric acrylamide-methacrylic acid ester compound (a), 2 to 25 parts by weight of the acid group-containing (meth)acrylic polymerizable monomer (b), 40 to 90 parts by weight of the hydrophobic crosslinkable polymerizable monomer (c), and 2 to 28 parts by weight of the hydrophilic monofunctional polymerizable monomer (f) as an optional component in 100 parts by weight of the total polymerizable monomers, and further containing 0.05 to 10 parts by weight of the photopolymerization initiator (d), 150 to 600 parts by weight of the filler (e), and 0.01 to 10 parts by weight of the polymerization accelerator (g) as an optional component with respect to 100 parts by weight of the total polymerizable monomers.

An even more preferred embodiment of the self-adhesive dental composite resin of the present invention is, for example, a self-adhesive dental composite resin containing 8 to 20 parts by weight of the asymmetric acrylamide-methacrylic acid ester compound (a), 4 to 20 parts by weight of the acid group-containing (meth)acrylic polymerizable monomer (b), 50 to 85 parts by weight of the hydrophobic crosslinkable polymerizable monomer (c), and 5 to 25 parts by weight of the hydrophilic monofunctional polymerizable monomer (f) as an optional component in 100 parts by weight of the total polymerizable monomers, and further containing 0.1 to 5 parts by weight of the photopolymerization initiator (d), 200 to 450 parts by weight of the filler (e), and 0.1 to 5 parts by weight of the polymerization accelerator (g) as an optional component with respect to 100 parts by weight of the total polymerizable monomers.

The conditions of the self-adhesive dental composite resins of the preferred embodiments, such as the types of the components and the contents thereof, can be selected or changed as appropriate within the ranges described above in the present description.

The self-adhesive dental composite resin of the present invention can be used, for example, as a filling material for restoration of broken or chipped tooth structure. In this case, the self-adhesive dental composite resin of the present invention can be applied directly to the tooth structure without using a pretreatment agent such as an etching agent, a primer, a self-etching primer, an adhesive, or the like. The self-adhesive dental composite resin of the present invention has excellent adhesiveness to tooth structures and excellent mechanical strength. In addition, detachment of the cured composite resin from the restored portion of a tooth or marginal leakage of the composite resin can be prevented.

The self-adhesive dental composite resin of the present invention has preferably a tensile bond strength to dentin of 9.5 MPa or more, more preferably 9.6 MPa or more, even more preferably 9.8 MPa or more, and particularly preferably 10.0 MPa or more. The self-adhesive dental composite resin of the present invention has preferably a flexural strength of 110 MPa or more, more preferably 115 MPa or more, even more preferably 119 MPa or more, and particularly preferably 120 MPa or more, when it cures to form a cured product. It is particularly preferable that the self-adhesive dental composite resin of the present invention have a tensile bond strength to dentin of 9.5 MPa or more and a flexural strength of 115 MPa or more when it cures to form a cured product.

The present invention encompasses embodiments obtainable by combining the above embodiments in various manners within the technical scope of the present invention as long as the effect of the present invention can be obtained.

EXAMPLES

Hereinafter, the present invention will be described in detail by way of examples and comparative examples. The present invention is not limited by these examples. Abbreviations used hereinafter are as follows.

[Asymmetric Acrylamide-methacrylic Acid Ester Compound (a)]

MAEA: N-methacryloyloxyethyl acrylamide (asymmetric acrylamide-methacrylic acid ester compound represented by the following formula):

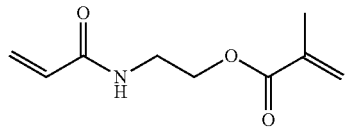

MAPA: N-methacryloyloxypropyl acrylamide (asymmetric acrylamide-methacrylic acid ester compound represented by the following formula):

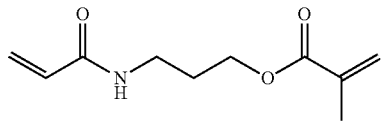

MAEEA: N-(1-ethyl-(2-methacryloyloxy)ethyl) acrylamide (asymmetric acrylamide-methacrylic acid ester compound represented by the following formula):

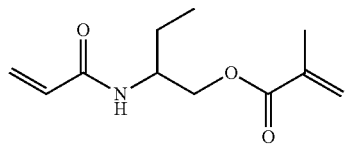

MAEGA: N-(2-(2-methacryloyloxyethoxy)ethyl) acrylamide (asymmetric acrylamide-methacrylic acid ester compound represented by the following formula):

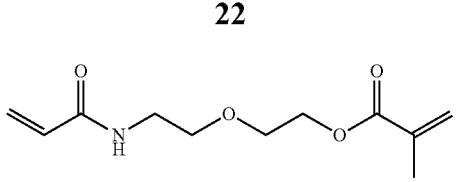

Hydrophilic Multifunctional (Meth)Acrylate-Based Polymerizable Monomer

MDMA: Mannitol dimethacrylate [3,4-di-O-methacryloyl-D-mannitol]

GDMA: Glycerol dimethacrylate

Symmetric (Meth)Acrylamide Compound

BAAE: Bisacrylamide ethylene

DEPBAA: N,N-diethyl-1,3-propylene-bisacrylamide

[Acid Group-containing (Meth)Acrylic Polymerizable Monomer (b)]

MDP: 10-methacryloyloxydecyl dihydrogen phosphate

4-META: 4-[2-(methacryloyloxy)ethoxycarbonyl] phthalic acid anhydride

[Hydrophobic Crosslinkable Polymerizable Monomer (c)]

Bis-GMA: 2,2-bis[4-(3-methacryloyloxy-2-hydroxypropoxy)phenyl]propane

D-2.6E: 2,2-bis(4-methacryloyloxypolyethoxyphenyl) propane (having an average number of moles of added ethoxy groups of 2.6)

TEGDMA: Triethylene glycol dimethacrylate

[Hydrophilic Monofunctional Polymerizable Monomer (f)]

Hydrophilic Monofunctional (Meth)Acrylamide-based Polymerizable Monomer

DEAA: N,N-diethylacrylamide

DMAA: N,N-dimethylacrylamide

Hydrophilic Monofunctional (Meth)Acrylate-based Polymerizable Monomer

HEMA: 2-hydroxyethyl methacrylate

GLM: 2,3-dihydroxypropyl methacrylate

[Polymerization Initiator (d)]

Photopolymerization Initiator

CQ: dl-camphorquinone

BAPO: Bis(2,4,6-trimethylbenzoyl)phenylphosphine oxide

[Polymerization Accelerator (g)]

DABE: Ethyl 4-(N,N-dimethylamino)benzoate

[Filler (e)]

Inorganic Filler 1: Silane-treated Silica Powder

Silica powder (manufactured by Nitchitsu Co., Ltd. under the trade name of Hi-Silica) was ground in a ball mill to obtain a pulverized silica powder. The average particle diameter of the pulverized silica powder thus obtained was measured using a laser diffraction particle size distribution analyzer (manufactured by Shimadzu Corporation, Model "SALD-2100"). As a result, the average particle diameter was 2.2 µm. 100 parts by weight of this pulverized silica powder was surface-treated with 4 parts by weight of γ-methacryloxypropyltrimethoxysilane by a conventional method. Thus, a silane-treated silica powder was obtained.

Inorganic Filler 2: Silane-treated Barium Glass Powder

Barium glass (manufactured by Esstech, Inc., Product code "E-3000") was ground in a ball mill to obtain a barium glass powder. The average particle diameter of the barium glass powder thus obtained was measured using a laser diffraction particle size distribution analyzer (manufactured by Shimadzu Corporation, Model "SALD-2100"). As a result, the average particle diameter was 2.4 µm. 100 parts by weight of this barium glass powder was surface-treated with 3 parts by weight of γ-methacryloxypropyltrimethoxysilane by a conventional method. Thus, a silane-treated barium glass powder was obtained.

[Others]

BHT: 2,6-di-t-butyl-4-methylphenol (stabilizer (polymerization inhibitor))

(Synthesis Example 1) Synthesis of MAEA 172.7 g (1.5 mol) of hydroxyethyl acrylamide (manufactured by Kohjin Film & Chemicals Co., Ltd.), 167 g (1.65 mol) of triethylamine, 38 mg (0.3 mmol) of p-methoxyphenol, and 1500 mL of anhydrous tetrahydrofuran were put into a 10-liter four-necked flask, stirred, and cooled to an internal temperature of −10° C. 700 mL of an anhydrous tetrahydrofuran solution of methacrylic acid chloride (172.5 g, 1.65 mol) was added dropwise at 5° C. or lower over 2 hours. After the dropwise addition of the solution, the resulting mixture was stirred for 24 hours under the conditions of room temperature. The resulting reaction solution was filtered, and insoluble matters were washed with ethyl acetate. The filtrate was concentrated under reduced pressure, and the residue was dissolved in ethyl acetate. The resulting solution was filtered with Celite to remove a small amount of insoluble matters, and then the filtrate was washed with a mixture of saturated saline solution and purified water (1:1). The organic layer was dried with anhydrous sodium sulfate, and then concentrated at 35° C. or lower under reduced pressure. The concentrated residue thus obtained was purified by silica gel column chromatography (developing solvent: ethyl acetate). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 201.2 g, and the percentage yield was 73.3%.

MS m/z: 184 (M+H)$^+$ $^1$H-NMR (270 MHz CDCl$_3$): δ1.94 (m, 3H), 3.62 (m, 2H), 4.28 (m, 2H), 5.58 (m, 1H), 5.66 (m, 1H), 6.08 (s, 1H), 6.10 (m, 1H), 6.11 (m, 1H), 6.28 (m, 1H) (ppm)

(Synthesis Example 2) Synthesis of MAPA 23.9 g (0.318 mol) of 3-aminopropanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

12.9 g (0.1 mol) of hydroxypropyl acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a white solid was obtained. The solid was subjected to LC-MS analysis and $^1$H-NMR measurement. It was determined from the locations and integrals of signals that the white solid thus obtained was a target compound. The weight yield was 11.1 g, and the percentage yield was 56.3%.

MS m/z: 198 (M+H)$^+$ $^1$H-NMR (270 MHz CDCl$_3$): δ1.93 (m, 2H), 1.97 (m, 3H), 3.42 (m, 2H), 4.27 (m, 2H), 5.58 (m, 1H), 5.65 (m, 1H), 6.11 (s, 1H), 6.10 (m, 1H), 6.13 (m, 1H), 6.30 (m, 1H) (ppm)

(Synthesis Example 3) Synthesis of MAEEA 28.3 g (0.318 mol) of DL-2-amino-1-butanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

14.3 g (0.1 mol) of N-(1-ethyl-(2-hydroxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 7.7 g, and the percentage yield was 36.3%.

MS m/z: 212 (M+H)$^+$ $^1$H-NMR (270 MHz DMSO-d$_6$): δ0.81 (m, 3H), 1.44 (m, 2H), 1.94 (m, 3H), 3.75 (m, 1H), 4.42 (m, 2H), 5.57 (m, 1H), 5.65 (m, 1H), 6.11 (m, 1H), 6.13 (m, 1H), 6.28 (m, 1H), 8.04 (s, 1H) (ppm)

(Synthesis Example 4) Synthesis of MAEGA 33.4 g (0.318 mol) of 2-(2-aminoethoxy)ethanol (manufactured by Tokyo Chemical Industry Co., Ltd.) and 400 mL of anhydrous tetrahydrofuran were put into a 1-liter four-necked flask, stirred, and cooled to an internal temperature of −10° C. 70 mL of an anhydrous tetrahydrofuran solution of acrylic acid chloride (14.4 g, 0.159 mol) was added dropwise at 5° C. or lower over 30 minutes. After the dropwise addition of the solution, the resulting mixture was stirred for 1 hour under the conditions of room temperature. After the reaction, insoluble matters were filtered and removed, and the filtrate was concentrated under reduced pressure. Thus, a pale yellow liquid was obtained.

15.9 g (0.1 mol) of N-(2-(2-hydroxyethoxy)ethyl)acrylamide obtained by the procedure described above, 200 mL of anhydrous tetrahydrofuran, and 15.2 g (0.15 mol) of triethylamine were put into a 500-milliliter four-necked flask, stirred, and cooled to an internal temperature of −10° C. 50 mL of an anhydrous tetrahydrofuran solution of methacrylic acid chloride (15.7 g, 0.15 mol) was added dropwise at 5° C. or lower over 30 minutes. After the dropwise addition of the solution, the resulting mixture was stirred for 3 hours under the conditions of room temperature. After the reaction, triethylamine hydrochloride was filtered and removed, and the filtrate was concentrated under reduced pressure. The concentrated residue thus obtained was purified by silica gel column chromatography (developing solvent:ethyl acetate/hexane=2/1). After the column purification, the solvent was removed under reduced pressure using a rotary evaporator. Thus, a pale yellow liquid was obtained. The liquid was subjected to LC-MS analysis and $^1$H-NMR measurement. It was determined from the locations and integrals of signals that the pale yellow liquid thus obtained was a target compound. The weight yield was 10.4 g, and the percentage yield was 45.8%.

MS m/z: 228 (M+H)$^+$ $^1$H-NMR (270 MHz DMSO-d$_6$): δ1.93 (m, 3H), 3.28 (m, 2H), 3.43 (m, 2H), 3.49 (m, 2H), 4.34 (m, 2H), 5.59 (m, 1H), 5.63 (m, 1H), 6.09 (m, 1H), 6.12 (m, 1H), 6.30 (m, 1H), 8.17 (s, 1H) (ppm)

BAAE

N,N'-ethylenebisacrylamide (manufactured by Alfa Aesar) was used.

DEPBAA

N,N-diethyl-1,3-propylene-bisacrylamide was synthesized according to the method disclosed in Example 2 of JP 2002-212019 A. Specifically, 36.3 g (0.40 mol) of acrylic acid chloride and 4 mg of monomethyl ether hydroquinone (MEHQ) were dissolved in 1.2 L of acetonitrile in a 2.5-liter sulfonation flask and cooled to −5° C. Next, 1.2 L of an acetonitrile solution of N,N'-diethylpropylene diamine (46.9 g, 0.36 mol) was added dropwise with stirring to keep the temperature between −5° C. and 0° C. 1.5 hours later, the temperature of the resulting mixture was raised to room temperature and then stirred for 4 hours. Next, the formed precipitate was filtered and washed with 0.5 L of acetonitrile. The acetonitrile phases were combined and concentrated under reduced pressure (10 mbar, 40° C.). The crude product was dissolved in 150 mL of acetone, filtered through a frit containing 50 g of silica gel 60, and then concentrated again. This process was repeated. As a result, 32.7 g (a percentage yield of 76%) of a pale yellow liquid (η (23° C.)=270 mPa·s) was obtained.

Examples 1 to 22 and Comparative Examples 1 to 4 and 6

The materials prepared in the above-mentioned synthesis examples were used. All the components shown in Table 1 to Table 3 except for the filler (e) (powder) were mixed at ordinary temperature, and the resulting homogeneous liquid components were each mixed with the filler (e) (powder) to prepare a self-adhesive dental composite resin. Next, the tensile bond strength to dentin and the flexural strength of the resulting cured product were measured by the following methods. Tables 1 to 3 each shows the content (parts by weight) of each component of this self-adhesive dental composite resin and the test results thereof.

Comparative Example 5

BAAE was used as a symmetric (meth)acrylamide compound instead of MAEA used in Example 1, and all the components shown in Table 3 except for the filler (e) (powder) were mixed at ordinary temperature. However, BAAE did not dissolve and thus a homogeneous composition could not be prepared.

[Measurement of Tensile Bond Strength to Dentin]

The labial surfaces of bovine mandibular incisors were each ground with #80 silicon carbide paper (manufactured by Nihon Kenshi Co., Ltd.) under running water to obtain samples with an exposed flat dentin surface. Each of the obtained samples was further ground with #1000 silicon carbide paper (manufactured by Nihon Kenshi Co., Ltd.) under running water. After the completion of grinding, each sample was dried by removing water from its surface by air-blowing. To the dried smooth surface was attached an about 150-μm-thick adhesive tape having a circular hole of 3-mm diameter, so that an adhesive area was defined.

The self-adhesive composite resin prepared in the manner as described above was applied within the circular hole, which was covered with a release film (made of polyester). Next, a glass slide was placed on and pressed against the release film to flatten the surface of the applied self-adhesive composite resin. Subsequently, the applied self-adhesive composite resin was cured by 10-second light irradiation through the release film using a dental visible light irradiation device (manufactured by Morita Corporation under the trade name "PenCure 2000").

Using a commercially-available dental resin cement (manufactured by Kuraray Noritake Dental Inc. under the trade name "PANAVIA 21"), a cylindrical stainless steel rod (with a diameter of 7 mm and a length of 2.5 cm) was bonded at its one end face (circular end face) to the surface of the obtained cured product of the self-adhesive composite resin. Thus, a sample was obtained. After the bonding, the sample was allowed to stand at room temperature for 30 minutes, after which the sample was immersed in distilled water. A total of 5 samples were prepared respectively for the bond test, and these samples were allowed to stand in a thermostat set at 37° C. for 24 hours.

The tensile bond strength of the above bond test samples was measured using a universal testing machine (manufactured by Shimadzu Corporation) with a crosshead speed set at 2 mm/minute. The average of the measured values of these samples was employed as the value of the tensile bond strength.

[Measurement of Flexural Strength of Cured Product]

A polyester film was placed over a glass slide and a stainless steel mold of 2 mm long, 25 mm wide, and 2 mm deep was placed on the film. Next, the self-adhesive composite resin was poured into the mold. A polyester film was placed on the resin in the mold and then a glass slide was further placed thereon and gently pressed against the polyester film. Both surfaces of the sample thus obtained were each irradiated with light for 2 minutes using a light irradiator for dental treatment ("α-light II" manufactured by J. Morita Tokyo Mfg. Corp.). Thus the resin was cured. A total of 5 cured products were prepared. The cured products were each removed from the mold, immersed in distilled water, and then allowed to stand in a thermostat at 37° C. for 24 hours. The flexural strength was measured using a universal testing machine (manufactured by Shimadzu Corporation) with a span of 20 mm and a crosshead speed of 1 mm/min. Five measurement samples were prepared in total. The average value of the measured values of these samples was employed as the value of the flexural strength.

[Mixed State Test Method for Liquid Component of Self-adhesive Dental Composite Resin]

When each paste of a self-adhesive dental composite resin was prepared, a liquid component prepared by mixing all the components other than the filler (e) (powder) at ordinary temperature was placed in a glass bottle and visually observed from outside the bottle to determine whether the liquid component was cloudy or even partially phase-separated so as to evaluate the mixed state. The cloudy or even partially phase-separated liquid components were determined to be "inhomogeneous" and the liquid components with no cloudiness nor phase separation were determined to be "homogeneous", and the former was rated "poor" and the latter was rated "good".

TABLE 1

| Components (parts by weight) | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|
| Asymmetric acrylamide-methacrylic acid ester compound (a) | MAEA | 10 | 15 | — | 10 | 10 | 10 | 10 | 10 | 3 | 6 | 22 |
| | MAPA | — | — | 10 | — | — | — | — | — | — | — | — |
| | MAEEA | — | — | — | — | — | — | — | — | — | — | — |
| | MAEGA | — | — | — | — | — | — | — | — | — | — | — |
| Acid group-containing (meth)acrylic polymerizable monomer (b) | MDP | 10 | 10 | 10 | — | 10 | 10 | 10 | 10 | 5 | 5 | 12 |
| | 4-META | — | — | — | 5 | — | — | — | — | — | — | — |
| Hydrophobic crosslinkable polymerizable monomer (c) | Bis-GMA | 30 | 30 | 30 | 30 | 30 | 30 | 30 | 30 | 30 | 30 | 30 |
| | D-2.6E | 10 | 10 | 10 | 15 | 10 | 10 | 10 | 10 | 10 | 10 | 10 |
| | TEGDMA | 30 | 35 | 30 | 30 | 30 | 30 | 30 | 30 | 42 | 39 | 16 |
| Hydrophilic monofunctional (meth)acrylamide-based polymerizable monomer (f) | DEAA | — | — | — | — | 10 | — | — | — | — | — | — |
| | DMAA | — | — | — | — | — | 10 | — | — | — | — | — |
| Hydrophilic monofunctional (meth)acrylate-based polymerizable monomer (f) | HEMA | 10 | — | 10 | 10 | — | — | 10 | 10 | 10 | 10 | 10 |
| Photopolymerization initiator (d) | CQ | — | — | — | — | — | — | 0.2 | — | — | — | — |
| | BAPO | 1 | 1 | 1 | 1 | 1 | 1 | — | 1 | 1 | 1 | 1 |
| Polymerization accelerator (g) | DABE | — | — | — | — | — | — | 0.4 | — | — | — | — |
| Polymerization inhibitor | BHT | 0.1 | 0.1 | 0.1 | 0.1 | 0.1 | 0.1 | 0.1 | 0.1 | 0.1 | 0.1 | 0.1 |
| Filler (e) | Inorganic filler 1 | 250 | 250 | 250 | 250 | 250 | 250 | 250 | — | 250 | 250 | 250 |
| | Inorganic filler 2 | — | — | — | — | — | — | — | 250 | — | — | — |
| Mixed state of liquid component | | good | good | good | good | good | good | good | good | good | good | good |
| Tensile bond strength to dentin (unit: MPa) | | 9.9 | 9.2 | 9.0 | 8.8 | 10.2 | 9.9 | 10.8 | 9.7 | 9.5 | 9.7 | 9.4 |
| Flexural strength of cured product (unit: MPa) | | 124 | 122 | 119 | 120 | 122 | 113 | 118 | 121 | 128 | 126 | 129 |

TABLE 2

| Components (parts by weight) | | Example 12 | Example 13 | Example 14 | Example 15 | Example 16 | Example 17 | Example 18 | Example 19 | Example 20 | Example 21 | Example 22 |
|---|---|---|---|---|---|---|---|---|---|---|---|---|
| Asymmetric acrylamide-methacrylic acid ester compound (a) | MAEA | 27 | 10 | 10 | 10 | 10 | 10 | 10 | 10 | 10 | — | — |
| | MAPA | — | — | — | — | — | — | — | — | — | — | — |
| | MAEEA | — | — | — | — | — | — | — | — | — | 10 | — |
| | MAEGA | — | — | — | — | — | — | — | — | — | — | 10 |
| Acid group-containing (meth)acrylic polymerizable monomer (b) | MDP | 10 | 1.5 | 3 | 25 | 10 | 10 | 10 | 10 | 10 | 10 | 10 |
| Hydrophobic crosslinkable polymerizable monomer (c) | Bis-GMA | 30 | 30 | 30 | 30 | 30 | 30 | 30 | 30 | 30 | 30 | 30 |
| | D-2.6E | 10 | 14.5 | 13 | — | 10 | 10 | 10 | 10 | 10 | 10 | 10 |
| | TEGDMA | 13 | 34 | 34 | 35 | 30 | 25 | 18 | 13 | 37 | 30 | 30 |
| Hydrophilic monofunctional (meth)acrylate-based polymerizable monomer (f) | HEMA | 10 | 10 | 10 | — | — | 15 | 22 | 27 | 3 | 10 | 10 |
| | GLM | — | — | — | — | 10 | — | — | — | — | — | — |
| Photopolymerization initiator (d) | BAPO | 1 | 1 | 1 | 1 | 1 | 1 | 1 | 1 | 1 | 1 | 1 |
| Polymerization inhibitor | BHT | 0.1 | 0.1 | 0.1 | 0.1 | 0.1 | 0.1 | 0.1 | 0.1 | 0.1 | 0.1 | 0.1 |
| Filler (e) | Inorganic filler 1 | 250 | 250 | 250 | 250 | 250 | 250 | 250 | 250 | 250 | 250 | 250 |
| Mixed state of liquid component | | good | good | good | good | good | good | good | good | good | good | good |
| Tensile bond strength to dentin (unit: MPa) | | 8.9 | 8.9 | 9.0 | 9.2 | 10.1 | 10.2 | 10.2 | 10.3 | 8.9 | 9.3 | 8.9 |
| Flexural strength of cured product (unit: MPa) | | 119 | 125 | 123 | 109 | 120 | 119 | 114 | 110 | 128 | 122 | 124 |

TABLE 3

| Components (parts by weight) | | Comparative Example 1 | Comparative Example 2 | Comparative Example 3 | Comparative Example 4 | Comparative Example 5 | Comparative Example 6 |
|---|---|---|---|---|---|---|---|
| Asymmetric acrylamide-methacrylic acid ester compound (a) | MAEA | 10 | — | — | — | — | — |
| Hydrophilic multifunctional (meth)acrylate-based polymerizable monomer | MDMA | — | — | — | 25 | — | — |
| | GDMA | — | — | 25 | — | — | — |
| Symmetric (meth)acrylamide compound | BAAE | — | — | — | — | 10 | — |
| | DEPBAA | — | — | — | — | — | 10 |
| Acid group-containing (meth)acrylic polymerizable monomer (b) | MDP | — | 10 | 10 | 10 | 10 | 10 |
| Hydrophobic crosslinkable polymerizable monomer (c) | Bis-GMA | 30 | 30 | 40 | 40 | 30 | 30 |
| | D-2.6E | 10 | 10 | — | — | 10 | 10 |
| | TEGDMA | 30 | 30 | — | — | 30 | 30 |
| Hydrophilic monofunctional (meth)acrylate-based polymerizable monomer (f) | HEMA | 20 | 20 | 25 | 25 | 10 | 10 |
| Photopolymerization initiator (d) | BAPO | 1 | 1 | 1 | 1 | 1 | 1 |
| Polymerization inhibitor | BHT | 0.1 | 0.1 | 0.1 | 0.1 | 0.1 | 0.1 |
| Filler (e) | Inorganic filler 1 | 250 | 250 | 250 | 250 | 250 | 250 |
| Mixed state of liquid component | | good | good | good | good | poor | good |
| Tensile bond strength to dentin (unit: MPa) | | 0 | 5.6 | 6.6 | 8.5 | NA | 6.5 |
| Flexural strength of cured product (unit: MPa) | | 133 | 109 | 124 | 80 | NA | 117 |

As shown in Table 1 and Table 2 above, each of the self-adhesive dental composite resins of the present invention (Examples 1 to 22) had a homogeneous composition, exhibited a tensile bond strength of 8.8 MPa or more to dentin, and further exhibited a flexural strength of 109 MPa or more when it cured to form a cured product.

As shown in Table 3, in Comparative Example 1 in which an acid group-containing (meth)acrylic polymerizable monomer was not used, adhesiveness to dentin was not obtained. In Comparative Example 2 in which an asymmetric acrylamide-(meth)acrylic acid ester compound (a) was not used, the tensile bond strength to dentin was 5.6 MPa.

In Comparative Example 3 in which GDMA as a hydrophilic multifunctional (meth)acrylate-based polymerizable monomer was used instead of MAEA used in Example 1, the tensile bond strength to dentin was 6.6 MPa. In Comparative Example 4 in which MDMA was used, the curability was not sufficient and the flexural strength of the cured product was 80 MPa.

BAAE as a symmetric (meth)acrylamide compound was used instead of MAEA used in Example 1 and all the components shown in Table 3 except for the filler (e) (powder) were mixed at ordinary temperature, but BAAE did not dissolve and thus a homogeneous composition could not be prepared, and the tensile bond strength to dentin and the flexural strength of the cured product could not be measured (Comparative Example 5). In Comparative Example 6 in which DEPBAA as a symmetric (meth)acrylamide compound was used, the tensile bond strength to dentin was 6.5 MPa due to the low hydrophilicity of DEPBAA.

INDUSTRIAL APPLICABILITY

The self-adhesive composite resin of the present invention can be used for treatment of a broken or chipped tooth or dental caries by first forming a cavity in the tooth and then injecting the resin directly into the cavity and photocuring it.

The invention claimed is:

1. A self-adhesive dental composite resin, comprising:
an asymmetric acrylamide-methacrylic acid ester compound (a);
an acid group-containing (meth)acrylic polymerizable monomer (b);
a hydrophobic crosslinkable polymerizable monomer (c);
a photopolymerization initiator (d); and
a filler (e),
wherein:
the asymmetric acrylamide-methacrylic acid ester compound (a) is represented by the following formula (1):

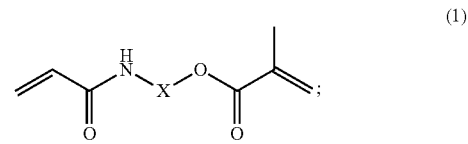

and
X is an optionally substituted, linear or branched $C_1$ to $C_6$ aliphatic group or an optionally substituted aromatic group, the aliphatic group is optionally interrupted by at least one linking group selected from the group consisting of —O—, —S—, —CO—, —CO—O—, —O—CO—, —NR$^1$—, —CO—NR$^1$—, —NR$^1$—CO—, —CO—O—NR$^1$—, —O—CO—NR$^1$—, and —NR$^1$—CO—NR$^1$—, and R$^1$ is a hydrogen atom or an optionally substituted, linear or branched $C_1$ to $C_6$ aliphatic group.

2. The self-adhesive dental composite resin according to claim 1, wherein X is an optionally substituted, linear or branched $C_1$ to $C_4$ aliphatic group.

3. The self-adhesive dental composite resin according to claim 1, wherein a content of the asymmetric acrylamide-methacrylic acid ester compound (a) is 2 to 30 parts by weight, a content of the acid group-containing (meth)acrylic polymerizable monomer (b) is 1 to 40 parts by weight, and a content of the hydrophobic crosslinkable polymerizable monomer (c) is 30 to 95 parts by weight in 100 parts by weight of the total polymerizable monomers.

4. The self-adhesive dental composite resin according to claim 1, further comprising a hydrophilic monofunctional polymerizable monomer (f).

5. The self-adhesive dental composite resin according to claim 4, wherein a content of the hydrophilic monofunctional polymerizable monomer (f) is 1 to 30 parts by weight in 100 parts by weight of the total polymerizable monomers.

6. The self-adhesive dental composite resin according to claim 1, wherein an acid group in the acid group-containing (meth)acrylic polymerizable monomer (b) is a phosphoric acid group or a carboxylic acid group.

7. The self-adhesive dental composite resin according to claim 1, wherein an acid group in the acid group-containing (meth)acrylic polymerizable monomer (b) is a phosphoric acid group.

8. The self-adhesive dental composite resin according to claim 1, being a one-part self-adhesive dental composite resin.

9. The self-adhesive dental composite resin according to claim 3, wherein the asymmetric acrylamide-methacrylic acid ester compound (a) is selected from the group consisting of N-methacryloyloxyethyl acrylamide, N-methacryloyloxypropyl acrylamide, N-(1-ethyl-(2-methacryloyloxy)ethyl) acrylamide, and N-(2-(2-methacryloyloxyethoxy)ethyl) acrylamide.

10. The self-adhesive dental composite resin according to claim 9, wherein the acid group-containing (meth)acrylic polymerizable monomer (b) is 10-methacryloyloxydecyl dihydrogen phosphate.

11. The self-adhesive dental composite resin according to claim 10, wherein the hydrophobic crosslinkable polymerizable monomer (c) comprises 2,2-bis[4-(3-methacryloyloxy-2-hydroxypropoxy)phenyl]propane, 2,2-bis(4-methacryloyloxypolyethoxyphenyl)propane and triethylene glycol dimethacrylate.

* * * * *